United States Patent [19]

Merce-Vidal et al.

[11] Patent Number: 5,731,331
[45] Date of Patent: Mar. 24, 1998

[54] TETRAHYDROPYRIDINE-(OR 4-HYDROXYPIPERIDINE) ALKYLAZOLES

[75] Inventors: Ramon Merce-Vidal; Jordi Frigola-Constansa, both of Barcelona, Spain

[73] Assignee: Laboratorios Del Dr. Esteve, S.A., Barcelona, Spain

[21] Appl. No.: 473,066

[22] Filed: Jun. 7, 1995

[30] Foreign Application Priority Data

Jul. 29, 1994 [FR] France .................. 94 09443

[51] Int. Cl.$^6$ ................................ A01N 43/40
[52] U.S. Cl. .................. 514/341; 514/322; 514/323; 514/326; 514/338; 514/339; 514/343; 546/199; 546/201; 546/210; 546/211
[58] Field of Search ............... 546/208, 210, 546/211, 199, 201; 514/322, 323, 326, 338, 339, 341, 343

[56] References Cited

U.S. PATENT DOCUMENTS

| | | | |
|---|---|---|---|
| 3,509,153 | 4/1970 | Hayao et al. | 544/366 |
| 3,994,904 | 11/1976 | Havera et al. | 546/194 |
| 4,539,407 | 9/1985 | Stack et al. | 546/87 |
| 4,675,403 | 6/1987 | Abou-Gharbia et al. | 544/230 |
| 4,754,038 | 6/1988 | Abou-Gharbia | 546/87 |
| 5,227,486 | 7/1993 | Merce-Vidal et al. | 544/295 |

FOREIGN PATENT DOCUMENTS

| | | |
|---|---|---|
| 0 441 349 A1 | 8/1991 | European Pat. Off. . |
| 0 497 658 A1 | 8/1992 | European Pat. Off. . |
| 0 497 659 A1 | 8/1992 | European Pat. Off. . |
| 20 17 265 | 10/1970 | Germany . |
| 26 32 870 | 2/1977 | Germany . |

OTHER PUBLICATIONS

J. Pharmacol. Exptl. Ther., vol. 148, No. 1, 1965 (pp. 54–65)—"Pharmacology of a Group of Phenylpiperazine Tetrazole Derivatives with Adrenergic Blocking Actions".
French Search Report of priority French patent application.

*Primary Examiner*—C. Warren Ivy
*Assistant Examiner*—Garth M. Dahlen
*Attorney, Agent, or Firm*—Dressler, Rockey, Milnamow & Katz, Ltd.

[57] ABSTRACT

The present invention relates to the compounds of general formula

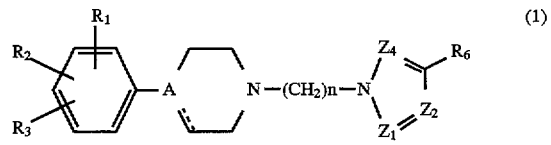

used as medicaments possessing therapeutic activity for the treatment of anxiety, psychosis, epilepsy, convulsion, motoricity problems, amnesia, cerebrovascular diseases or senile dementia.

2 Claims, No Drawings

TETRAHYDROPYRIDINE-(OR 4-HYDROXYPIPERIDINE) ALKYLAZOLES

The present invention relates to new 4-aryltetrahydropyridines and 4-arylpiperidinols linked to alkyl-azoles of general formula (I)

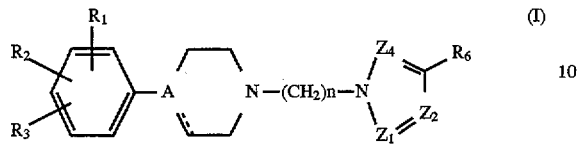

and to their physiologically acceptable salts, to the processes for their preparation, to their application as medicaments and to the pharmaceutical compositions which contain them.

The compounds which are the subjects of the invention can also be used in the pharmaceutical industry as intermediates and for the preparation of medicaments.

These compounds possess a powerful affinity for sigma and/or 5-$HT_{1A}$ receptors and are therefore potentially useful in the treatment of certain psychic and neurological disorders of human beings and other meals.

Phenomena exist which involve sigma receptors in the treatment of psychosis. Many atypical antipsychotics, such as rimcazole (Schwarcz, G. et al., Drug Dev. Res., 1985, 5, 387), remoxipride (Wadworth, A. N. et al., Drugs 1990, 40, 863) or thiospirone (Jain, A. K. et al., Int. Clin. Psychopharmacol. 1987, 2, 129), show a significant affinity for sigma receptors.

Moreover, studies of the biology and function of sigma receptors indicate that ligands for the sigma receptor can be effective in the treatment of certain motor disorders, in particular Huntington's chorea, dystonia and Tourette's syndrome. The presence of sigma receptors in the substantia nigra makes it possible to use them in the treatment of Parkinson's disease (Walker, J. M. et al., Pharmacological Reviews, 1990, 42, 355).

Certain ligands for sigma receptors are involved in the modulation of the effects produced by the intervention of the NMDA receptor and act as antiischemic agents in in vivo tests (Rao, T. S. et al., Molecular Pharmacology, 1990, 37, 978), with the possibility of use as neuroprotectors and in the treatment of epilepsy and of convulsion (Kaiser C., Neurotransmissions VII, 1991).

It has been said that ligands for sigma receptors exhibit antiamnesic effects in animal models (Early et al., Brain Research, 1991, 546, 281).

Sigma ligands influence the levels of acetylcholine in animal models (Matsuno et al., Brain Research 1992, 575, 315) and can consequently be used in the treatment of senile dementia, for example of Alzheimer type.

Ligands for 5-$HT_{1A}$ receptors, in particular agonists or partial agonists for 5-$HT_{1A}$, show a proven anxiolytic and antidepressant activity (Glitz, D. A., Drugs, 1991, 41, 11).

Consequently, agents having a powerful affinity for sigma and/or 5-$HT_{1A}$ receptors can be used in one or a number of the treatments indicated.

Examples of 4-aryl-1,2,3,6-tetrahydropyridines and of 4-aryl-4-hydroxypiperidines are found in the bibliography; however, compounds in which these sub-structures are joined to the nitrogen of an azole ring by means of an unsubstituted alkyl chain are not found to be described:

Davis L. Temple et al., U.S. Pat. No. 4,320,131; 16 Mar. 1982.

Richard A. Glennon et al., J. Med. Chem., 1991, 34, 3360–65.

Jean-Luc Malleron et al., J. Med. Chem., 1991, 34; 8, 2477–83.

Henning Böttcher et al., J. Med. Chem., 1992, 35, 4020–26.

Zhuihua Sui et al., Synthesis,. 1993, 803–8.

David I. Schuster et al., J. Med. Chem., 1993, 36, 3923–28.

David J. Wustrow et al., BioMed. Chem. Lett., 1993, 3, 277–80.

Shimazaki Norihiko et al., Can. Pat. App., CA 2053475AA.

The Inventors have previously described a series of N-alkylazoles joined to the nitrogen of various heterocycles which are useful as non-benzodiazepine agents in the treatment of anxiety (European Patents No. EP 382637, EP 497659 and EP 502786) and in the treatment of other behavioral disorders (European Patents EP 429360 and EP 497658). Descriptions are given in the cited patents of the compounds of general formula (I) in which A represents, in all cases, a nitrogen atom and it consequently concerns a piperazine ring. In the present invention, the piperazine ring is replaced by a piperidine or a tetrahydropyridine.

The compounds which are the subjects of the invention correspond to the general formula (I)

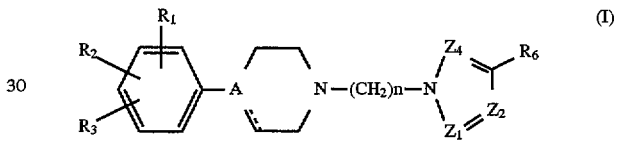

in which $R_1$, $R_2$ and $R_3$, which are identical or different, each represent a hydrogen atom, a halogen atom, a linear or branched alkyl radical, an aryl or substituted aryl radical or an alkoxyl radical. Moreover, two adjacent radicals can form a saturated or aromatic ring.

A represents a carbon atom and the dotted line represents an additional bond or else A represents a carbon atom bonded to a hydroxyl group (C—OH) and the dotted line represents the absence of an additional bond.

n can have values ranging from 2 to 6

$Z_1$ represents a nitrogen atom or a substituted carbon atom which can be represented by C—$R_4$ $Z_2$ represents a nitrogen atom or a substituted carbon atom which can be represented by C—$R_5$ $Z_4$ represents a nitrogen atom or a substituted carbon atom which can be represented by C—$R_7$ $R_4$, $R_5$, $R_6$ and $R_7$, which are identical or different, represent a hydrogen atom, a halogen atom, a linear or branched alkyl radical, a hydroxyl radical, an alkoxyl radical, a carboxyl radical, a carboxamide radical, an alkyl carboxylate radical or an aryl or substituted aryl radical or else two adjacent radicals can form part of another ring, which may or may not be aromatic.

The invention also relates to the physiologically acceptable salts of the compounds of general formula (I), in particular the salts of hydrochloric, hydrobromic, sulfuric, phosphoric, acetic, lactic, malonic, succinic, glutaric, fumaric, malic, tartaric, citric, ascorbic, maleic, benzoic, phenylacetic, cinnamic and salicylic acids and of alkane-, cycloalkane- or arenesulfonic acids.

The new derivatives of general formula (I) can be prepared according to the following processes:

Process A

By reaction of a spiran derivative of general formula (II)

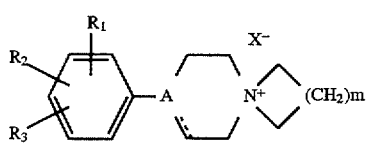

in which

R$_1$, R$_2$, R$_3$ and A have the meaning indicated above, m can have values ranging from 0 to 4 and X represents a leaving group, such as chloro, bromo, mesyloxy or tosyloxy, with a nitrogenous heterocycle of general formula (III)

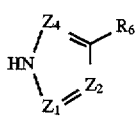

in which

Z$_1$, Z$_2$, Z$_4$ and R$_6$ have the meaning indicated above.

The reaction is carried out in a solution of dimethyl sulfoxide, dimethylformamide, an alcohol such as ethanol, an aromatic hydrocarbon such as toluene or an aliphatic hydrocarbon such as hexane or an ether such as dioxane. This reaction is preferably carried out in the presence of a base such as potassium carbonate or triethylamine.

The reaction temperature varies between room temperature and the reflux temperature of the solvent used.

The reaction times vary between 1 and 24 hours.

Process B

By simultaneous "one pot" reaction between a derivative of general formula (IV), an alkylating agent of general formula (V) and a nitrogenous heterocycle of general formula (III).

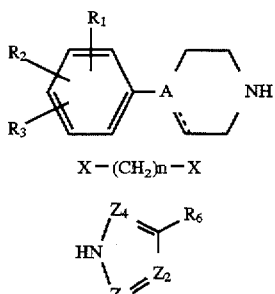

X—(CH$_2$)n—X (V)

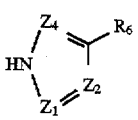

where

R$_1$, R$_2$, R$_3$, A, X, n, Z$_1$, Z$_2$, Z$_4$ and R$_6$ have the meaning given above.

The reaction is carried out in a solution of dimethyl sulfoxide, dimethylformamide, an alcohol such as ethanol, an aromatic hydrocarbon such as toluene or an aliphatic hydrocarbon such as hexane or an ether such as dioxane. This reaction is preferably carried out in the presence of a base such as potassium carbonate or triethylamine.

The reaction temperature varies between room temperature and the reflux temperature of the solvent used.

The reaction times vary between 1 and 24 hours.

Process C

The preparation of the compounds of general formula (I) can be carried out by reaction, under alkylation conditions, of the amines of general formula (IV)

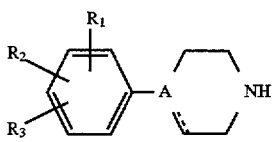

in which

R$_1$, R$_2$, R$_3$ and A have the meaning given above, with compounds of general formula (VI)

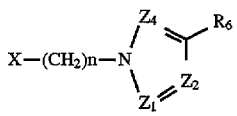

in which

X, n, Z$_1$, Z$_2$, Z$_4$ and R$_6$ have the meaning indicated above.

The reaction is carried out in a solution of dimethyl sulfoxide, dimethylformamide, an alcohol such as ethanol, an aromatic hydrocarbon such as toluene or an aliphatic hydrocarbon such as hexane or an ether such as dioxane. This reaction is preferably carried out in the presence of a base such as potassium carbonate or triethylamine.

The reaction temperature varies between room temperature and the reflux temperature of the solvent used.

The reaction times vary between 1 and 24 hours.

Process D

The compounds of general formula (I) can be prepared by reaction, under alkylation conditions, of a compound of general formula (VII)

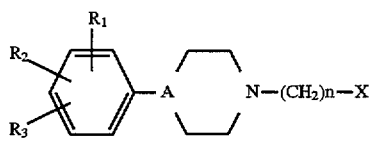

in which

R$_1$, R$_2$, R$_3$, n and A have the meaning indicated above with a nitrogenous heterocycle of general formula (III)

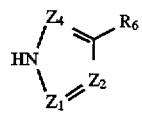

in which

Z$_1$, Z$_2$, Z$_4$ and R$_6$ have the meaning given above.

The reaction is carried out in a solution of dimethyl sulfoxide, dimethylformamide, an alcohol such as ethanol, an aromatic hydrocarbon such as toluene or an aliphatic hydrocarbon such as hexane or an ether such as dioxane. This reaction is preferably carried out in the presence of a base such as potassium carbonate or triethylamine.

The reaction temperature varies between room temperature and the reflux temperature of the solvent used.

The reaction times vary between 1 and 24 hours.

Process E

By dehydration of compounds of general formula (I)

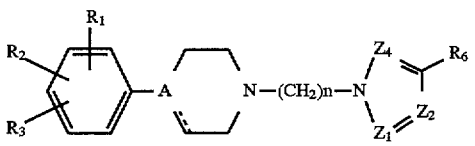

in which

R$_1$, R$_2$, R$_3$, n, Z$_1$, Z$_2$, Z$_4$ and R$_6$ have the meaning indicated above, A represents a carbon atom linked to a hydroxyl group (C—OH) and the dotted line represents the absence of any additional bond.

The reaction is carried out in acid medium, such as, for example, hydrochloric acid, trifluoroacetic acid, sulfuric acid or phosphoric acid, or by treatment with thionyl chloride in benzene.

The reaction temperature varies between room temperature and 180° C.

The reaction times vary between 1 and 14 hours.

Process F

By addition of organometallic reagents, for example phenyllithium or phenylmagnesium bromide, to compounds of general formula (VIII)

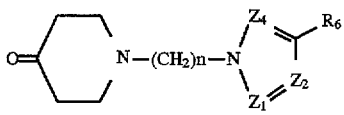

in which n, $Z_1$, $Z_2$, $Z_4$ and $R_6$ have the meaning given above.

The reaction is carried out in a solution of an inert solvent, generally an ether such as, for example, dimethoxyethane, tetrahydrofuran or ethyl ether.

The reaction temperature varies between room temperature and the reflux temperature of the solvent used.

The reaction times vary between 5 minutes and 24 hours.

Process G

By reduction of the carbonyl of the amide group of compounds of general formula (IX)

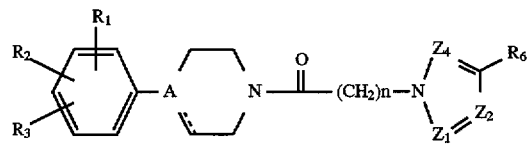

in which $R_1$, $R_2$, $R_3$, A, n, $Z_1$, $Z_2$, $Z_4$ and $R_6$ have the meaning indicated above.

The reaction is preferably carried out in an inert organic solvent, such as ethyl ether or tetrahydrofuran, with reducing agents such as $LiAlH_4$, $AlH_3$ or diborane.

The reaction temperature varies between room temperature and the reflux temperature of the solvent used.

The reaction times vary between 5 minutes and 24 hours.

Process H

The corresponding salt is obtained by reaction of a compound of general formula (I) with a nontoxic inorganic or organic acid in a suitable solvent, which can be, for example, an alcohol such as methanol, ethanol or any one of the propanols or butanols, an ester such as ethyl acetate or a nitrile such as acetonitrile, and by using conventional techniques for precipitation, crystallization, and the like.

The inorganic acid is chosen, inter alia, from hydrochloric, hydrobromic, sulfuric and phosphoric acids and the organic acid is chosen from mono-, di- or tricarboxylic acids, such as, for example, acetic, lactic, malonic, succinic, glutaric, fumaric, malic, tartaric, citric, ascorbic, maleic, benzoic, phenylacetic, cinnamic and salicylic acids, and alkane-, cycloalkane- or arenesulfonic acids.

The mono- or disalts of the acid can be formed and these salts can be in the anhydrous or hydrated form.

The invention is made clearer by the following examples, given simply by way of information, it being understood that they can in no way limit the specific conditions of the process nor the scope of the invention.

PROCESS A

EXAMPLE 1

Preparation of 4-chloro-1-[4-(4-hydroxy-4-phenyl-1-piperidyl)butyl]-1H-pyrazole.

A mixture of 15.0 g (48 mmol) of 8-hydroxy-8-phenyl-5-azoniaspiro[4,5]decane, 5.4 g (53 mmol) of 4-chloropyrazole and 13.2 g of potassium carbonate in 200 ml of dimethylformamide is heated at reflux for 20 hours. Evaporation to dryness is then carried out at reduced pressure, the residue is redissolved in chloroform and washing is carried out repeatedly with water. The organic phase is dried with anhydrous sodium sulfate and evaporation is carried out at reduced pressure, a crude product being obtained which is suspended in ethyl ether, which is filtered while cold and which is washed with ethyl ether. 12.4 g (37.1 mmol) of 4-chloro-1-[4-(4-hydroxy-4-phenyl-1-piperidyl)butyl]-1H-pyrazole are obtained.

The melting point and the spectroscopic data for the identification of this product are provided in Table I.

PROCESS B

EXAMPLE 7

Preparation of 4-chloro-1-[4-[4-hydroxy-4-(3-trifluoromethylphenyl)-1-piperidyl]butyl]-1H-pyrazole.

A mixture of 8.6 g (35 mmol) of 4-hydroxy-4-(3-trifluoromethylphenyl)-1-piperidine, 7.68 g of 1,4-dibromobutane and 13.8 g of potassium carbonate in 100 ml of dimethylformamide is heated at reflux for 4 hours. 3.59 g (35 mmol) of 4-chloropyrazole are then added and the reaction mixture is maintained at reflux for 14 hours. Evaporation to dryness is then carried out at reduced pressure, the residue is redissolved in chloroform and washing is carried out repeatedly with water. The organic phase is dried with anhydrous sodium sulfate and evaporated at reduced pressure, a crude product being obtained which is purified by chromatography on silica gel. 9.7 g (24.2 mmol) of 4-chloro-1-{4-[4-hydroxy-4-(3-trifluoromethylphenyl)-1-piperidyl]butyl}-1H-pyrazole are obtained.

The spectroscopic data for the identification of this product are found in Table I.

PROCESS C

EXAMPLE 14a

Preparation of 1-[4-(4-phenyl-1,2,3,6-tetrahydro-1-pyridyl)butyl]indole.

A mixture of 4.8 g (30 mmol) of 4-phenyl-1,2,3,6-tetrahydropyridine, 6.22 g of 1-(4-chlorobutyl)indole and 8.3 g of potassium carbonate in 100 ml of dimethylformamide is heated at 90° C. for 3 hours. Evaporation to dryness is then carried out at reduced pressure, the residue is redissolved in chloroform and washing is carried out repeatedly with water. The organic phase is dried with anhydrous sodium sulfate and evaporation is carried out at reduced pressure, a crude product being obtained which is purified by chromatography on silica gel. 5.7 g (17.3 mmol). of 1-[4-(4-phenyl-1,2,3,6-tetrahydro-1-pyridyl)butyl]indole are obtained.

The spectroscopic data for the identification of this product are found in Table II.

PROCESS D

EXAMPLE 21a

Preparation of 4-chloro-1-[3-(4-phenyl-1,2,3,6-tetrahydro-1-pyridyl)propyl]-1H-pyrazole.

A solution of 2.05 g (20 mmol of 4-chloropyrazole in dimethylformamide is added dropwise to a suspension of 1.0 g of NaH in dimethylformamide. The white suspension is heated for 30 minutes at 100° C. Cooling is carried out and 4.7 g (20 mmol) of 1-(3-chloropropyl)-4-phenyl-1,2,3,6-tetrahydropyridine, dissolved in dimethylformamide, are added. Heating is carried out at reflux for 2 hours. Evaporation to dryness is then carried out and the residue is extracted with chloroform, washed with water and dried with sodium sulfate. The resulting crude product is purified by chromatography on silica gel. 5.2 g (17.2 mmol) of 4-chloro-1-[3-(4-phenyl-1,2,3,6-tetrahydro-1-pyridyl)propyl]-1H-pyrazole are obtained.

The spectroscopic data for the identification of this product are provided in Table II.

PROCESS E

EXAMPLE 2a

Preparation of 1-[4-(4-phenyl-1,2,3,6-tetrahydro-1-pyridyl)butyl]-1H-benzimidazole.

A solution of 13.4 g (38.2 mmol) of 1-[4-(4-hydroxy-4-phenyl-1-piperidyl)butyl]-1H-benzimidazole, 150 ml of concentrated HCl and 75 ml of ethanol is heated at reflux for 6 hours. The ethanol is then evaporated and the aqueous solution is cooled, basified with dilute NaOH and extracted with chloroform. The organic phase is dried with anhydrous sodium sulfate and evaporated at reduced pressure, a crude product being obtained which is purified by chromatography on silica gel. 9.1 g (27.5 mmol) of 1-[4-(4-phenyl-1,2,3,6-tetrahydro-1-pyridyl)butyl]-1H-benzimidazole are obtained.

The melting point and the spectroscopic data for the identification of this product are provided in Table II.

PROCESS F

Example 11

Preparation of 4,5-dichloro-1-{4-[4-hydroxy-4-(4-methylphenyl)-1-piperidyl]butyl}-2-methyl-1H-imidazole.

A solution of 1.0 g (3.3 mmol) of 4,5-dichloro-2-methyl-1-[4-(4-oxo-1-piperidyl)butyl]-1H-imidazole in 10 ml of anhydrous tetrahydrofuran is added to a suspension of 1.08 g (11.4 mmol) of $MgCl_2$ in 15 ml of anhydrous THF at −40° C. and under a nitrogen atmosphere. The mixture is stirred for 5 minutes and then, at −40° C., 6.8 ml of a 1.0M solution of 4-methylphenylmagnesium bromide are added. The resulting suspension is stirred for 15 minutes at −40° C. and for 3 hours at room temperature. An aqueous ammonium chloride solution is then added and the tetrahydrofuran is evaporated. The resulting aqueous phase is extracted with chloroform. The chloroform phase is washed with water, dried with anhydrous sodium sulfate and evaporated to dryness, a crude product being obtained which is purified by chromatography on silica gel, giving 1.02 g (2.6 mmol) of 4,5-dichloro-1-{4-[4-hydroxy-4-(4-methylphenyl)-1-piperidyl]butyl}-2-methyl-1H-imidazole.

The spectroscopic data for the identification of this product are found in Table I.

PROCESS G

EXAMPLE 16a

Preparation of 1-[4-(4-phenyl-1,2,3,6-tetrahydro-1-pyridyl)butyl]-1H-pyrazole.

2.0 g of $LiAlH_4$ are added to a solution of 3.3 g (10 mmol) of 1-[4-(4-phenyl-1,2,3,6-tetrahydro-1-pyridyl)-3-oxobutyl]-1H-pyrazole in 25 ml of THF. The resulting mixture is refluxed for 2 hours. The excess $LiAlH_4$ is destroyed by addition of concentrated NaOH and water. The inorganic salts are filtered off and the THF is evaporated under vacuum, giving 2.6 g (8.2 mmol) of 1-[4-(4-phenyl-1,2,3,6-tetrahydro-1-pyridyl)butyl]-1H-pyrazole.

The melting point and the spectroscopic data for the identification of this product are found in Table II.

PROCESS H

EXAMPLE 11a

Preparation of the hydrochloride of 4,5-dichloro-2-methyl-1-[4-(4-phenyl-1,2,3,6-tetrahydro-1-pyridyl)butyl]-1H-imidazole.

2.5 ml of an 8.4N hydrochloric acid/ethanol solution are added to a solution, cooled in an ice bath, of 7.4 g (20.3 mmol) of 4,5-dichloro-2-methyl-1-[4-(4-phenyl-1,2,3,6-tetrahydro-1-pyridyl)butyl]-1H-imidazole in 15 ml of absolute ethanol. After a few minutes, a precipitate appears which is filtered, washed with cold ethanol and dried, 7.7 g (19.2 mmol) of 4,5-dichloro-2-methyl-1-[4-(4-phenyl-1,2,3,6-tetrahydro-1-pyridyl)-butyl]-1H-imidazole hydrochloride being obtained.

The melting point and the spectroscopic data for the identification of this product are found in Table II.

TABLE I

| Ex | R$_1$ | R$_2$ | R$_3$ | R$_4$ | R$_5$ | Z$_1$ | Z$_2$ | Z$_4$ | R$_6$ | n | M.p. | IR cm$^{-1}$ | $^1$H NMR (300 MHz), δ(solvent) |
|---|---|---|---|---|---|---|---|---|---|---|---|---|---|
| 1 | H | H | H | H | H | N | CH | CH | Cl | 4 | 102–103° C. | 3364(b.a. OH), 2950, 2810, 1375, 1130, 991, 969, 760, 696, 605 KBr | 1.56(quin, J=7.1Hz, 2H); 1.65(b.a. 1H); 1.76(d, J=12.4Hz, 2H); 1.90(quin, J=7.6Hz, 2H); 2.20(m, 2H); 2.40–2.55(a.c., 4H); 2.83(d, J=9.5Hz, 2H); 4.11(t, J=7Hz, 2H); 7.21–7.42(a.c., 5H); 7.52(d, J=8.5Hz, 2H) (CDCl$_3$) |
| 2 | H | H | H | H | H | C—CH$_3$ | N | CCl | Cl | 4 | 86–89° C. | 3196(b.a., OH), 2951, 2924, 2824, 1406, 1247, 1146, 762, 703 KBr | 1.59(m, J=5.3 J=6.6, 2H); 1.70–1.32(a.c., 4H); 2.16(d, t, J=13.0Hz J=4.4Hz, 2H); 2.37(s, 3H); 2.41–2.55(a.c., 5H); 2.79(d, J=11.3Hz, 2H); 3.88(t, J=7.5Hz, 2H); 7.27(t, J=7.2Hz, 1H); 7.36(t, J=7.6Hz, 2H); 7.51(d, J=7.3Hz, 2H)(CDCl$_3$) |
| 3 | H | H | H | H | H | CH | N | CH=CH—CH=CH—C | 4 | 122–123° C. | 3180(b.a.,OH), 2929, 2818, 1496, 1467, 1459, 1445, 1286, 1219, 1143, 769, 743, 707 KBr | 1.51(quin, J=7.4Hz, 2H); 1.73(d, J=12.7Hz, 2H); 1.87(quin, J=7.6Hz, 2H); 2.10(dt, J=12.9Hz J=4.1Hz, 2H); 2.36–2.50(a.c., 4H); 2.70(d, J=11.2Hz, 2H); 3.25(b.a., 1H); 4.12(t, J=7.1Hz, 2H); 7.21–7.40(a.c., 6H); 7.51(d, J=8.3Hz, 2H); 7.70–7.75(a.c., 2H) (CDCl$_3$) |
| 4 | H | H | H | H | H | CH | N | N | H | 4 | 123° C. | 3180(b.a., OH), 2949, 2919, 2838, 1276, 1145, 1135, 1006, 770, 707, 676 KBr | 1.45(quin, J=7.5Hz, 2H); 1.69(d, J=12.9Hz, 2H); 1.85(quin, J=7.5Hz, 2H); 2.07(dt, J=13.0Hz J=4.1Hz, 2H); 2.33–2.45(a.c., 4H); 2.69(d, J=11.2Hz, 2H); 2.93(b.a., 1H); 4.10(t, J=6.9Hz, 2H); 7.18(t, J=7Hz, 1H); 7.27(t, J=7.8Hz, 2H); 7.46(d, J=8.3Hz, 2H); 7.80(s, 1H); 7.91(s, 1H)(CDCl$_3$) |
| 5 | H | H | Cl | H | H | CH | CH | CH | Cl | 4 | 106° C. | 3145(b.a., OH), 2947, 2918, 2834, 1318, 1147, 1083, 1112, 990, 817, 612 KBr | 1.47(quin, J=7.5Hz, 2H); 1.69(d, J=11.9Hz, 2H); 1.84(quin, J=7.6Hz, 2H); 2.05(dt, J=13Hz, J=4.4Hz, 2H); 2.34–2.50(a.c., 5H); 2.72(d, J=11.2Hz, 2H); 4.05(t, J=7.0Hz, 2H); 7.29(syst. AB, J=8.6Hz, 2H); 7.36(s, 2H); 7.42 (lsyst AB, J=8.6Hz, 2H)(CDCl$_3$) |
| 6 | H | H | Cl | H | H | C—CH$_3$ | N | CCl | Cl | 4 | oil | 3340(b.a., OH), 2946, 2820, 1537, 1492, 1471, 1406, 1376, 1247, 1135, 1094, 1013, 828, 755 film | 1.54(m, 2H); 1.67–1.78(a.c., 4H); 2.06(dt, J=13Hz, J=4.2Hz, 2H); 2.32(s, 3H); 2.38–2.45(a.c., 5H); 2.73(d, J=11.2Hz, 2H); 3.86(t, J=7.3Hz, 2H); 7.28(syst AB, J=8.6Hz, 2H); 7.43–7.51(a.c., 2H); 7.66(d, J=7.5Hz, 1H) (CDCl$_3$) |
| 7 | H | CF$_3$ | H | H | H | N | CH | CH | Cl | 4 | oil | 3360(b.a., OH), 2948, 2823, 1438, 1378, 1330, 1212, 1165, 1124, 1047, 972, 804, 704 | 1.48(quin, J=7.6Hz, 2H; 1.71(d, J=12.5Hz, 4H); 1.85(quin, J=11.5Hz, 2H); 2.06–2.21(a.c., 3H); 2.36–2.43(a.c., 4H); 2.76(d, J=7.1Hz, 2H); 7.35(s, 2H); 7.43–7.51(a.c., 2H); 7.66(d, J=7.5Hz, 2H)(CDCl$_3$) |

TABLE I-continued

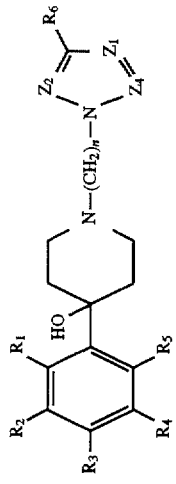

| | R1 | R2 | R3 | R4 | R6 | Z1 | Z2 | Z4 | n | m.p. | IR | NMR |
|---|---|---|---|---|---|---|---|---|---|---|---|---|
| 8 | H | CF3 | H | H | C—CH3 | N | CCl | Cl | 4 | oil | film 3340(b.a., OH), 2948, 2823, 1408, 2335(s, 3H); 2.40–2.52(a.c, 4H); 2.80(d, J=11.7Hz, 2H); 1330, 1165, 1126, 1075, 789, 763, 704 | 1.57(quin, J=7.5Hz, 2H); 1.70–1.80(a.c, 4H); 2.15(dt, J=3.6Hz, 2H); 3.88(t, J=7.0Hz, 2H); 7.42–7.57(a.c., 2H); 7.69(d, J=7.5Hz, 1H); 7.82(s, 1H)(CDCl3) |
| 9 | H | H | F | H | C—CH3 | N | CCl | Cl | 4 | oil | film 3330(b.a., OH), 2946, 2818, 1509, 1406, 1247, 1222, 1160, 835 | 1.58(m, 2H); 1.64–1.81(a.c., 4H); 2.14(dt, J=12.9Hz J=3.6Hz 2H); 2.32(s, 3H); 2.43–2.60(a.c., 4H); 2.84(d, J=11Hz, 2H); 3.87(t, J=7.1Hz, 2H); 4.18 (b.a., 1H); 7.01(t, J=8.8Hz, 2H); 7.46(dd, J=5.2Hz, 2H)(CDCl3) |
| 10 | H | H | H | H | CH | CH | CH=CH—CH=CH—C | | 4 | 109–111° C. | KBr 3190(b.a., OH), 2956, 2823, 1461, 1446, 1319, 1303, 1218, 1142, 738, 703 | 1.57(m, 2H); 1.73(d, J=14Hz, 2H); 1.80(b.a., 1H); 1.90(m, 2H); 2.13(dt, J=13Hz J=4Hz, 2H); 2.32–2.46(a.c., 4H); 2.76(d, J=11.3Hz, 2H); 2.77(d, J=11.2Hz, 2H); 6.50(d, J=3.1Hz, 2H); 7.05–7.14(a.c., 2H); 7.18–7.40(a.c., 5H); 7.50(d, J=7.8Hz, 2H); 7.00(d, J=7.3Hz, 1H)(CDCl3) |
| 11 | H | CH3 | H | H | C—CH3 | N | CCl | Cl | 4 | oil | film 3360(b.a., OH), 2946, 2818, 1535, 1471, 1406, 1376, 1247, 1134, 817, 755 | 1.53(m, 2H); 1.66–1.84(a.c., 4H); 2.09(dt, J=12.9Hz, 2H); 2.33(s, 3H); 2.36(s, 3H); 2.39–2.50(a.c., 4H); 3.87(t, J=7.0Hz, 2H); 7.15(syst AB, J=7.8Hz, 2H); 7.33(syst AB, J=7.8Hz, 2H)(CDCl3) |
| 12 | H | H | H | H | CH | N | CH | CH | 4 | 89–91° C. | KBr 3137(b.a., OH), 2947, 2532, 1396, 1378, 1119, 1046, 756, 697 | 1.51(quin, J=7.6Hz, 2H); 1.73(d, J=12.3Hz, 2H); 2.00–2.20(a.c., 3H); 2.35–2.45(a.c., 4H); 2.76(d, J=10.2Hz, 2H); 1.89(quin, J=7.6Hz, 2H); 4.13(t, J=7.1Hz, 2H); 6.21(s, 1H); 7.21(m, 1H); 7.30–7.37 (a.c., 3H); 7.44–7.52(a.c., 5H)(CDCl3) |
| 13 | H | H | H | H | CH | N | CH=CH—CH=CH—C | | 4 | 107–109° C. | KBr 3311(b.a., OH), 2953, 2803, 1465, 1375, 1133, 1117, 1043, 1017, 761, 744, 704 | 1.53(m, 2H); 1.71(d, J=12.2Hz, 2H); 1.95(m, 2H); 2.10(m, 2H); 2.29(b.a., 1H); 2.35–2.47(a.c., 4H); 2.71(d, J=7.1Hz, 2H); 4.39(t, J=7.1Hz, 2H); 7.13(t, J=8.3Hz, 1H); 7.22–7.44(a.c., 5H); 7.50(d, J=8Hz, 2H); 7.71(d, J=8.3Hz, 1H); 7.95(s, 1H)(CDCl3) |
| 14 | H | H | H | H | C—CH=CH—CH=CH | CH | CH | | 4 | 120–122° C. | KBr 3295(b.a., OH), 2946, 2817, 1377, 1126, 786, 735, 700 | 1.58(m, 2H); 1.73(d, J=13.5Hz, 2H); 1.90–2.20(a.c., 5H); 2.38–2.47(a.c., 4H); 2.75(d, J=10.5Hz, 2H); 4.42(t, J=6.6Hz, 2H); 7.06(t, J=7.5Hz, 1H); 7.22–7.37(a.c., 4H); 7.49(d, J=7.8Hz, 2H); 7.61–7.71(a.c., 2H); 7.90(s, 1H)(CDCl3) |
| 15 | H | CH3 | H | H | CH | N | CH | Cl | 4 | 81–82° C. | KBr 3122(b.a., OH), 2936, 1475, 1434, 1378, 1319, 989, | 1.51(quin, J=7.6Hz, 2H); 1.87(quin, J=7.6Hz, 2H); 2.12(dt, J=12.8Hz J=4.4Hz, 2H); 2.33(s, 3H); 2.35–2.48(a.c., 5H); 2.74(t, J=7.1Hz, 2H); 4.07(t, J=11.2Hz, 2H); 7.15(d, J=8Hz, 2H); |

TABLE I-continued

| Ex | R₁ | R₂ | R₃ | R₄ | R₅ | Z₁ | Z₂ | Z₄ | R₆ | n | Salt/M.p. | IR cm⁻¹ | ¹H NMR(300 MHz), δ, J=Hz(solvent) |
|---|---|---|---|---|---|---|---|---|---|---|---|---|---|
| 16 | H | H | CH₃O | H | H | N | CH | CH | Cl | 4 | 122–123° C. | 3190(b.a., OH) 2954, 2923, 2827, 1509, 1314, 1243, 1178, 971 KBr | 1.49(quin, J=7.6Hz, 2H); 1.72(d, J=11.8Hz, 2H); 1.84(quin, J=7.4Hz, 2H); 2.00–2.14(a.c.(dt+b.a.), 3H); 2.34–2.47(a.c., 4H); 2.72(d, J=11Hz, 2H); 3.77(s, 3H); 4.05(t, J=7.1Hz, 2H); 6.85(d, J=9Hz, 2H); 7.24–7.42 (a.c., 4H)(CDCl₃) |
| 17 | H | H | H | H | CPh | N | N | CH | Cl | 4 | 108–110° C. | 3220(b.a., OH) 2944, 2817, 1473, 1446, 1421, 1136, 1046, 787, 773, 761, 700 film | 1.45(quin, J=7.6Hz, 2H); 1.68–1.82(a.c., 4H); 2.08(dt, J=13.0Hz, J=4.1Hz, 2H); 2.29–2.42(a.c., 4H); 2.51(b.a., 1H); 2.67(d, J=11.2Hz, 2H); 4.01 m(t, J=7.3Hz, 2H); 7.01(s, 1H); 7.08(s, 1H); 7.20–7.56(a.c., 10H)(CDCl₃) |
| 18 | H | H | CH₃ | H | H | CH=CH–CH=CH–C | | N | Cl | 4 | oil | 3260(b.a., OH) 2944, 2817, 1497, 1459, 1381, 1287, 1135, 1046, 817, 745 film | 1.58(quin, J=7.6Hz, 2H); 1.74(d, J=12Hz, 2H); 1.82(b.a, 1H); 1.95(quin, J=7.6Hz, 2H); 2.11(dt, 2H); 2.33(s, 3H); 2.40–2.50(a.c., 4H); 2.74(d, J=11.5Hz, 2H); 4.20(t, J=7.1Hz, 2H); 7.15(d, J=8.3Hz, 2H); 7.22–7.35 (a.c., 3H); 7.37–7.43(a.c., 2H); 7.79(m, 1H); 7.87(s, 1H)(CDCl₃) |
| 19 | H | H | H | H | H | N | | CPh | Cl | 4 | 138–139° C. | 3194(b.a., OH) 2939, 3806, 1509, 1446, 773, 766, 758, 696 film | 1.38(m, 2H); 1.56(m, 2H); 1.72(d, J=12.4Hz, 2H); 2.09(dt, 2H); 2.25(t, J=7.4Hz, 2H); 2.39(m, 2H); 2.66(m, 2H); 3.10(b.a, 1H); 3.78(t, J=7.2Hz, 2H); 7.10–7.52(a.c., 16H); |
| 20 | CH=CH–CH=CH | | H | H | H | N | CH | CH | Cl | 4 | oil | 3357(b.a., OH) 2946, 2833, 1434, 1379, 1315, 1140, 1123, 972, 781, 613 KBr | 1.44(quin, J=7.5Hz, 2H); 1.77(quin, J=7.5Hz, 2H); 2.15–2.30(a.c., 5H); 2.34(t, J=7.5Hz, 2H); 2.57(m, 2H); 2.73(d, J=11.3Hz, 2H); 3.99(t, J=7.1Hz, 2H); 7.26–7.46(a.c., 6H); 7.73(d, J=8.1Hz, 1H); 7.82(m, 1H); 8.91(m, 1H)(CDCl₃) |
| 21 | H | CH=CH–CH=CH | | H | H | N | CH | CH | Cl | 4 | 142–143° C. | 3131(b.a., OH) 2950, 2820, 1377, 1311, 971, 829, 761, 613 KBr | 1.55(quin, J=7.5Hz, 2H); 1.70–1.97(a.c., 5H); 2.29(dt, J=12.7Hz, J=4.1Hz, 2H); 2.41–2.55(a.c., 4H); 2.83(d, J=11.7Hz, 2H); 4.11(t, J=7.0Hz, 2H); 7.39–7.50(a.c., 4H); 7.64(dd, J=9.1Hz, J=1.5Hz, 1H); 7.81–7.85(a.c., 3H); 7.95(s, 1H)(CDCl₃) |
| 22 | H | H | H | H | H | N | CH | CH | 4-Cl-C₆H₄ | 4 | 137–140° C. | 3347, 2944, 2810, 1562, 1492, 1376, 1127, 1094, 1002, 952, 828, 760, 699 KBr | 1.56(m, 2H); 1.74(m, 2H); 1.80(b.a, 1H); 1.94(m, 2H); 2.40(dt, J=13.1Hz, J=4.0Hz, 2H); 2.40–2.50(a.c., 4H); 2.77(m, 2H); 4.15(t, J=7.0Hz, 2H); 7.25–7.40(a.c., 7H); 7.50(d, J=8.3Hz, 2H); 7.61(s, 1H); 7.72(s, 1H)(CDCl₃) |

TABLE I-continued

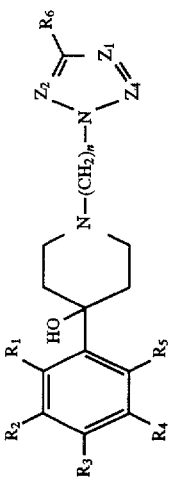

| | $R_1$ | $R_2$ | $R_3$ | $R_4$ | $R_5$ | $R_6$ | $Z_1$-$Z_2$-$Z_3$-$Z_4$ | n | salt | m.p. | IR (cm$^{-1}$) | $^1$H NMR |
|---|---|---|---|---|---|---|---|---|---|---|---|---|
| 23 | H | H | F | H | H | CH | CH=CH—CH=CH—C | N | | 120-122° C. | 3230, 2947, 2915, 1504, 1219, 1135, 835, 746 KBr | 1.58(m, 2H); 1.70(m, 2H); 1.93(m, 2H); 2.12(m, 2H); 2.40-2.55(a.c., 4H); 2.76(m, 2H); 4.19(t, J=7.0Hz, 2H); 7.02(m, 2H); 7.26(m, 2H); 7.30-7.50(a.c., 3H); 7.74(m, 1H); 7.83(s, 1H)(CDCl$_3$) |
| 24 | H | CCF$_3$ | H | H | H | N | CH=CH—CH=CH—C | CH | 4 | HCl 147-148° C. | 3259, 2465, 2420, 2365, 1328, 1108, 1073 KBr | 1.62-1.84(a.c., 6H); 2.53(m, 2H); 3.09-3.40(a.c., 6H); 4.12(t, J=6.8Hz, 2H); 5.76(s, 1H); 7.51(s, 1H); 7.52-7.82(a.c., 4H); 8.02(s, 1H); 10.96(b.a., 1H)(DMSO-d$_6$) |
| 25 | H | H | F | H | H | N | CH=CH—CH=CH—C | CH | 4 | | 136-137° C. | 3303, 2951, 2805, 1506, 1464, 1376, 1218, 1162, 1118, 832, 741 KBr | 1.54(m, 2H); 1.60-1.80(a.c., 3H); 1.97(m, 2H); 2.06(dt, J=4.3Hz, 2H); 2.30-2.43(a.c. 4H; 2.72(m, 2H); 4.40(t, J=7.0Hz, 2H); 6.99(t, J=8.8Hz, 2H); 7.12(m, 1H); 7.32-7.47(a.c., 4H); 7.71(d, J=8.1Hz, 1H); 7.96(s, 1H)(CDCl$_3$—CD$_3$OD[1:1]) |
| 26 | H | H | F | H | H | N | C—CH=CH—CH=CH | CH | 4 | | 148-150° C. | 3325, 2950, 2923, 2812, 1509, 1377, 1218, 1131, 834, 758 | 1.57(m, 2H); 1.70-1.77(a.c., 3H); 1.98-2.19(a.c., 4H); 2.35-2.49(a.c., 4H); 2.77(d, J=11.2Hz, 2H); 4.45(t, J=7.0Hz, 2H); 6.98-7.15(a.c., 3H); 7.25-7.49(a.c., 3H); 7.63(d, J=8.3Hz, 1H); 7.69(d, J=7.8Hz, 1H); 7.91 (s, 1H)(CDCl$_3$—CD$_3$OD[1:1]) |
| 27 | H | H | F | H | H | N | C—CH=CH—CH=CH | N | 4 | | 109-110° C. | 3400, 2931, 2812, 1509, 1229, 1101, 831, 745 KBr | 1.47-1.80(a.c., 4H); 1.90-2.25(a.c., 5H); 2.30-2.55(a.c., 4H); 2.70(m, 2H); 4.78(t, J=6.9Hz, 2H); 7.01(t, J=8.7Hz, 2H); 7.26-7.54(a.c., 4H); 7.85(dd, J=6.7Hz, J=3.0Hz, 2H)(CDCl$_3$—CD$_3$OD[1:1]) |
| 28 | H | H | F | H | H | N | CH=CH—CH=CH—C | N | 4 | | 102-103° C. | 3430, 2952, 2925, 1508, 1223, 1140, 833, 744 KBr | 1.45-1.80(a.c., 4H); 1.85-2.25(a.c., 5H); 2.25-2.55(a.c., 4H); 2.77 (m, 2H); 4.69(t, J=6.9Hz, 2H); 7.01(t, J=8.7Hz, 2H); 7.26-7.53(a.c., 5H); 8.06(d, J=7.3Hz, 1H)(CDCl$_3$—CD$_3$OD[1:1]) |

TABLE II

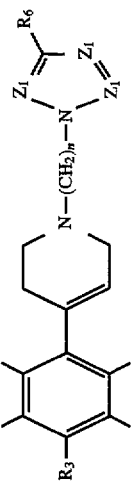

| Ex | $R_1$ | $R_2$ | $R_3$ | $R_4$ | $R_5$ | $Z_1$ | $Z_2$ | $R_6$ | $Z_4$ | n | M.p. | IR cm$^{-1}$ | $^1$H NMR(300 MHz), δ(solvent) |
|---|---|---|---|---|---|---|---|---|---|---|---|---|---|
| 1a | H | H | H | H | H | N | CH | Cl | CH | 4 | 62–64° C. | 3113, 2920, 2745, 1375, 1325, 1138, 965, 837, 742, 688 KBr | 1.56(quin, J=7.6Hz, 2H); 1.91(quin, J=7.6Hz, 2H); 2.47 (t, J=7.4Hz, 2H); 2.58(m, 2H); 2.65(t, J=5.6Hz, 2H); 3.14 (m, 2H); 4.11(t, J=7.1Hz, 2H); 6.06(m, 1H); 7.23–7.42 (a.c., 7H)(CDCl$_3$) |
| 2a | H | H | H | H | H | CH | N | CH=CH–CH=CH–C | 4 | 66–69° C. | 2933, 1495, 745, 694, 665 film | 1.55(quin, J=7.6Hz, 2H); 1.92(quin, J=7.6Hz, 2H); 2.43 (t, J=7.3Hz, 2H); 2.52(m, 2H); 2.61(t, J=5.6Hz, 2H); 3.07 (m, 2H); 4.14(t, J=7.1Hz, 2H); 6.02(m, 1H); 7.20–7.40 (a.c., 8H); 7.80(m, 1H); 7.86(s, 1H)(CDCl$_3$) |
| 3a | H | H | H | H | H | CH | N | H | N | 4 | 63–64° C. | 2942, 1438, 1381, 1271, 1142, 1006, 753, 697, 681, KBr | 1.56(m, 2H); 1.95(m, 2H); 2.47(t, J=7.1Hz, 2H); 2.56 (m, 2H); 2.66(t, J=5.3Hz, 2H); 3.11(m, 2H); 4.19 (t, J=7.0Hz, 2H); 6.05(s, 1H); 7.21(m, 1H); 7.30 (t, J=7.6Hz, 2H); 7.36(d, J=7.8Hz, 2H); 7.94(s, 1H); 8.06 (s, 1H)(CDCl$_3$) |
| 4a | H | H | Cl | H | H | N | CH | Cl | CH | 4 | 103–104° C. | 2939, 1493, 1436, 1381, 1306, 1122, 1097, 973, 843, 824, 730 | 1.54(m, 2H); 1.90(m, 2H); 2.45(t, J=7.4Hz, 2H); 2.51 (m, 2H); 2.65(t, J=5.6Hz, 2H); 3.10(m, 2H); 4.10 (t, J=7.0Hz, 2H); 6.03(m, 1H); 7.26(syst AB, J=8.6Hz, 2H); 7.29(syst AB, J=8.6Hz, 2H); 7.37(s, 1H); 7.41 (s, 1H)(CDCl$_3$) |
| 5a | H | H | Cl | H | H | C–CH$_3$ | N | Cl | CCl | 4 | 119–120° C. | 2922, 1531, 1494, 1469, 1403, 1380, 1366, 1245, 10–94, KBr | 1.59(m, 2H); 1.76(m, 2H); 2.36(s, 3H); 2.42–2.53(a.c., 4H); 2.67(t, J=5.3Hz, 2H); 3.12(m, 2H); 3.88(t, J=7.4Hz, 2H); 6.04(m, 1H); 7.27(syst AB, J=9.1Hz, 2H); 7.30 (syst AB, J=9.1Hz, 2H)(CDCl$_3$) |
| 6a | H | CF$_3$ | H | H | H | N | CH | Cl | CH | 4 | oil | 2944, 1434, 1375, 1331, 1247, 1165, 1126, 1076, 972, 800 698 KBr | 1.53(quin, J=7.5Hz, 2H); 1.89(quin, J=7.7Hz, 2H); 2.45 (t, J=7.3Hz, 2H); 2.54(m, 2H); 2.66(t, J=5.5Hz, 2H); 3.10 (m, 2H); 4.08(t, J=7.1Hz, 2H); 6.10(m, 1H); 7.35–7.56 (a.c., 5H); 7.59(s, 1H)(CDCl$_3$) |
| 7a | H | CF$_3$ | H | H | H | C–CH$_3$ | N | Cl | CCl | 4 | oil | 2931, 2815, 1533, 1405, 1331, 1246, 1165, 1125, 1076, 797, 699 film | 1.62(quin, J=6.6Hz, 2H); 1.77(quin, J=7.6Hz, 2H); 2.37 (s, 3H); 2.51(t, J=7.2Hz, 2H); 2.60(m, 2H); 2.71 (t, J=5.6Hz, 2H); 3.17(m, 2H); 3.89(t, J=7.3Hz, 2H); 6.14 (m, 1H); 7.40–7.50(a.c., 2H); 7.55(d, J=7.5Hz, 1H); 7.62 (s, 1H)(CDCl$_3$) |
| 8a | H | H | F | H | H | N | CH | Cl | CH | 4 | 86–87° C. | 2936, 1512, 1378, 1326, 1229, 988, 967 KBr | 1.60(quin, J=7.5Hz, 2H); 1.91(quin, J=5.6Hz, 2H); 2.50–2.82(a.c., 4H); 2.76(t, J=5.6Hz, 2H); 3.19(m, 2H); 4.11(t, J=6.9Hz, 2H); 5.97(s, 1H); 6.99(t, J=8.8Hz, 2H); 7.32(dd, J=8.8Hz, J=5.4Hz, 2H); 7.38(s, 1H); 7.40(s, 1H) (CDCl$_3$) |
| 9a | H | H | F | H | H | C–CH$_3$ | N | Cl | CCl | 4 | 79–82° C. | 2934, 1531, 1512, 1408, 1247, 1225, 1167, 818 | 1.59(m, 2H); 1.76(m, 2H); 2.37(s, 3H); 2.48(t, J=7.2Hz, 2H); 2.54(m, 2H); 2.67.99 (t, J=5.6Hz, 2H); 3.12(m, 2H); 3.89(t, J=7.3Hz, |

TABLE II-continued

| | | | | | | | | mp/state | IR | NMR |
|---|---|---|---|---|---|---|---|---|---|---|
| 10a | H | H | H | C—CH₃ | N | Cl | | CCl₄ | oil | 2929, 1533, 1405, 1246, 748 film | 2H); 5.99(m, 1H); 6.99(t, J=8.7Hz, 2H); 7.33 (dd, J=8.7Hz J=5.4Hz, 2H)(CDCl₃) |
| 11a | H | H | H | C—CH₃ | N | Cl | | CCl₄ | HCl 203–204°C. | 2930, 2576, 1407, 1376, 1245, 750, KBr | 1.59(m, 2H); 1.76(m, 2H); 2.37(s, 3H); 2.49(t, J=7.3Hz, 2H); 2.58(m, 2H); 2.69(t, J=5.4Hz, 2H); 3.14(m, 2H); 3.89(t, J=7.4Hz, 2H); 6.06(m, 1H); 7.22–7.40(a.c., 5H) (CDCl₃) |
| 12a | H | H | H | C—CH₃ | N | Cl | | CCl₄ | HCl 192–194° C. | 3569, 2941, 2692, 2556, 1601, 1446, 769, 753, 698 KBr | 1.69(m, 2H); 1.81(m, 2H); 2.35(s, 3H); 2.71(d, J=7.2Hz, 1H); 2.91(m, 1H); 3.17(a.c., 3H); 3.56(m, 1H); 3.75 (m, 1H); 3.90–3.97(a.c., 3H); 6.17(s, 1H); 7.25–7.40 (a.c., 3H); 7.47(d, J=7.6Hz, 2H); 11.30(b.a., 1H) (DMSO-d₆) |
| 13a | H | F | H | CH | CH | CH=CH—CH=CH—C | | | oil | 2937, 1510, 1464, 1230, 1161, 816, 742 film | 1.67(m, 2H); 1.79(m, 2H); 2.36(s, 3H); 2.69(d, J=18.0Hz, 1H); 2.88(m, 1H); 3.15(a.c., 3H); 3.54(m, 1H); 3.72 (m, 1H); 3.85–3.98(a.c., 3H); 6.15(s, 1H); 7.22–7.38(a.c., 3H); 7.45(d, J=7.3Hz, 2H); 9.93(b.a., 1H); 11.36(b.a., 1H) (DMSO-d₆) |
| 14a | H | H | H | CH | CH | CH=CH—CH=CH—C | | | oil | 2938, 1510, 1485, 1463, 1446, 1376, 1336, 1315, 763, 740, 695 | 1.61(quin, J=7.6Hz, 2H); 1.93(quin, J=7.6Hz, 2H); 2.42–2.58(a.c., 4H); 2.66(t, J=5.6Hz, 2H); 3.11(m, 2H); 4.17(t, J=7.0Hz, 2H); 5.98(m, 1H); 6.51(d, J=3.9Hz, 1H); 6.95–7.39(a.c., 8H); 7.65(d, J=7.8Hz, 1H)(CDCl₃) 1.63(quin, J=7.4Hz, 2H); 1.94(quin, J=7.4Hz, 2H); 2.49 (t, J=7.6Hz, 2H); 2.60(m, 2H); 2.69(t, J=5.3Hz, 2H); 3.14 (m, 2H); 4.19(t, J=7.1Hz, 2H); 6.08(m, 1H); 6.53(m, 1H); 7.08–7.44(a.c., 9H); 7.67(d, J=8.1Hz, 1H)(CDCl₃) |
| 15a | H | CH₃ | H | C—CH₃ | N | Cl | | CCl₄ | 87–88° C. | 2939, 2916, 1529, 1404, 1378, 1243, 1166, 1131, 1016 film | 1.59(m, 2H); 1.75(m, 2H); 2.32(s, 3H); 2.36(s, 3H); 2.47(t, J=7.2Hz, 2H); 2.54(m, 2H); 2.67(t, J=5.2Hz, 2H); 3.11(m, 2H,); 3.87(t, J=7.3Hz, 2H); 6.01(s, 1H); 7.11 (syst AB, J=8.1Hz, 2H); 7.27(syst AB, J=8.1Hz, 2H)(CDCl₃) |
| 16a | H | H | H | CH | N | H | | CH₄ | 36–38° C. | 2941, 1396, 748, 695 film | 1.54(quin, J=7.6Hz, 2H); 1.91(quin, J=7.6Hz, 2H); 2.45 (t, J=7.6Hz, 2H); 2.55(m, 2H); 2.65(t, J=5.6Hz, 2H); 3.11 (m, 2H); 4.14(t, J=7.1Hz, 2H); 6.03(m, 1H); 6.21(m, 1H); 7.20–7.39(a.c., 6H); 7.49(m, 1H)(CDCl₃) |
| 17a | H | H | H | CH | N | CH=CH—CH=CH—C | | CH₄ | 50–52° C. | 2942, 1465, 1158, 832, 740, 691 KBr | 1.61(quin, 2H); 2.00(quin, J=7.5Hz, 2H); 2.43–2.58(a.c., 4H); 2.68(m, 2H); 3.14(s, 2H); 4.43(t, J=6.6Hz, 2H); 6.02 (s, 1H); 7.13(t, J=7.3Hz, 1H); 7.20–7.51(a.c., 7H); 7.73 (d, J=7.9Hz, 1H) 7.99(s, 1H)(CDCl₃) |
| 18a | H | H | H | C—CH=CH—CH=CH | N | CH | | CH | 73–75° C. | 3049, 2940, 2778, 1467, 1371, 1158, 1143, 1131, 757, 742, 692 KBr | 1.60(quin, 2H); 2.09(quin, J=7.4Hz, 2H); 2.48 (t, J=7.4Hz, 2H); 2.55(m, 2H); 2.66(t, J=5.6Hz, 2H); 3.11 (d, J=2.9Hz, 2H); 4.45(t, J=7.1Hz, 2H); 6.03(s, 1H); 7.07 (t, J=7.5Hz, 1H); 7.20–7.39(a.c., 6H); 7.63(d, J=4.3Hz, 1H); 7.70(d, J=8Hz, 1H); 7.91(s, 1H)(CDCl₃) |
| 19a | H | CH₃ | H | CH | CH | Cl | | CH | 72–73° C. | 3115, 2938, 2740, 1376, 1328, 1137, 986, 966, 844, 824 797 KBr | 1.55(quin, 2H); 1.90(quin, J=7.5Hz, 2H); 2.33(s, 3H); 2.46(t, J=7.4Hz, 2H); 2.55(m, 2H); 2.66(t, J=6.4Hz, 2H); 3.11(m, 2H); 4.10(t, J=7.0Hz, 2H); 6.01(s, 1H); 7.12 (syst AB, J=8Hz, 2H); 7.27(syst AB, J=8Hz, 2H) 7.37(s, 1H)(CDCl₃) |
| 20a | H | CH₃O | H | CH | CH | Cl | | CH | 104–105° C. | 2923, 1533, 1405, 1379, 1246, 749 KBr | 1.54(quin, 2H); 1.89(quin, J=7.6Hz, 2H); 2.44(t, J=7.4Hz, 2H); 2.52(m, 2H); 2.65(t, J=5.3Hz, 2H); 3.10(m, 2H); 3.78(s, 3H); 4.09(t, J=7.0Hz, 2H); 5.95(s, 1H); 6.84 (syst AB, J=8.5Hz, 2H); 7.31(syst AB, J=8.5Hz, 2H) |

TABLE II-continued

| Ex | R₁ | R₂ | R₃ | R₄ | R₅ | Z₁ | Z₂ | R₆ | Z₄ | n | Salt/M.p. | IR cm⁻¹ | ¹H NMR(300 MHz), δ, J=Hz(solvent) |
|---|---|---|---|---|---|---|---|---|---|---|---|---|---|
| 21a | H | H | H | H | H | N | CH | Cl | CH | 3 | oil | 2948, 2923, 2811, 2774, 1446, 1382, 1316, 971, 748, 695 film | 7.36(s, 1H); 7.40(s, 1H)(CDCl₃) 2.08(quin, J=7.0Hz, 2H); 2.42(t, J=7.0Hz, 2H); 2.58 (m, 2H); 2.67(t, J=5.6Hz, 2H); 3.13(m, 2H); 4.17 (t, J=6.9Hz, 2H); 6.07(m, 1H); 7.23–7.45(a.c., 7H)(CDCl₃) |
| 22a | H | H | H | H | H | N | N | Cl | CCl | 3 | oil | 2923, 1533, 1405, 1379, 1246, 749 | 1.95(quin, J=7.2Hz, 2H); 2.39(s, 3H); 2.46(t, J=7.0Hz, 2H); 2.58(m, 2H); 2.69(t, J=4.9Hz, 2H); 3.13(m, 2H); 3.96(t, J=7.3Hz, 2H); 6.07(m, 1H); 7.20–7.41(a.c., 5H) (CDCl₃) |
| 23a | H | H | H | CCH₃ | H | N | N | Cl | CH | 4 | oil | 2940, 1496, 1474, 1445, 1379, 1275, 774, 698 film | 1.51(m, 2H); 1.81(m, 2H); 2.40(t, J=7.4Hz, 2H); 2.56 (m, 2H); 2.63(t, J=4.9Hz, 2H); 3.09(m, 2H); 4.04(t, J=7.2Hz, 2H); 6.03(m, 1H); 7.03(m, 1H); 7.13(m, 1H); 7.22–7.48(a.c., 8H); 7.58(m, 2H)(CDCl₃) |
| 24a | H | H | CH₃ | CPh | H | N | N | H | CH=CH–CH=CH–C | 4 | 90–91° C. | 2939, 2915, 1500, 1461, 1377, 1365, 750 KBr | 1.59(m, 2H); 1.95(m, 2H); 2.32(s, 3H); 2.46(t, J=7.3Hz, 2H); 2.53(m, 2H); 2.63(t, J=5.5Hz, 2H); 3.08(m, 2H); 4.20(t, J=6.95Hz, 2H); 6.00(s, 1H); 7.11(d, J=7.8Hz, 2H); 7.27(a.c., 4H); 7.40(m, 1H); 7.80(m, 1H); 7.89(s, 1H) (CDCl₃) |
| 25a | H | H | H | H | H | CH | N | Ph | CPh | 4 | 100–101° C. | 3130, 2939, 2770, 1600, 1506, 1443, 1259, 954, 780, 774, 750, 696, 649 KBr | 1.46(quin, J=7.5Hz, 2H); 1.65(quin, J=7.6Hz, 2H); 2.33 (t, J=7.3Hz, 2H); 2.53(m, 2H); 2.60(m, 2H); 3.05(m, 2H); 3.84(t, J=7.2Hz, 2H); 6.02(m, 1H); 7.05–7.50(a.c., 15H); 7.61(s, 1H)(CDCl₃) |
| 26a | CH=CH–CH=CH | H | H | H | N | CH | Cl | CH | 4 | oil | 3057, 3043, 2942, 2806, 2768, 1378, 1365, 971, 801, 778 film | 1.61(quin, J=7.5Hz, 2H); 1.95(quin, J=7.6Hz, 2H); 2.51–2.57(a.c., 4H); 2.76(t, J=5.6Hz, 2H); 3.20(m, 2H); 4.14(t, J=7.1Hz, 2H); 5.74(m, 1H); 7.26–7.50(a.c., 6H); 7.75(d, J=8Hz, 1H); 8.02(m, 1H); (CDCl₃) |
| 27a | H | CH=CH–CH=CH | H | H | N | CH | Cl | CH | 4 | 95–96° C. | 3111, 2920, 2806, 1374, 1326, 966, 826, 749, 612, KBr | 1.57(m, 2H); 1.92(m, 2H); 2.48(m, 2H); 2.71 (a.c., 4H); 3.18(m, 2H); 4.11(m, 2H); 6.22(m, 1H); 7.38–7.50(a.c., 4H); 7.61(m, 1H); 7.75–7.84(a.c., 4H); (CDCl₃) |
| 28a | H | H | F | H | H | CH | N | CH=CH–CH=CH–C | 2 | 135–136° C. | 3050, 2920, 2780, 2760, 1510, 1492, 1459, 1224, 1202, 1161, 771, 751 KBr | 2.54(m, 2H); 2.74(t, J=5.6Hz, 2H); 2.92(t, J=6.7Hz, 2H); 3.24(m, 2H); 4.35(t, J=6.7Hz, 2H); 5.98(m, 1H); 7.00 (t, J=8.7Hz, 2H); 7.26–7.40(a.c., 4H); 7.42(m, 1H); 7.81 (m, 1H); 8.01(s, 1H)(CDCl₃) |
| 29a | H | H | H | H | H | CH | N | CH=CH–CH=CH–C | 4 | HCl 177–178° C. | 2940, 2488, 1500, 1420, 1390, 742 KBr | 1.70–1.90(a.c., 4H); 2.78(m, 2H); 3.17(m, 2H); 3.20–3.50(b.a., 4H); 3.79(m, 2H); 4.30(td, J=6.6Hz, 2H); 6.15(m, 1H); 7.17–7.40(a.c., 5H); 7.45(d, J=7.3Hz, 2H); 7.65(m, 2H); 8.35(s, 1H)(DMSO-d₆) |
| 30a | H | H | F | H | H | CH | N | CH=CH–CH=CH–C | 4 | 106–108° C. | 2942, 1512, 1498, 1460, 1376, 1221, 756 KBr | 1.59(quin, J=7.5Hz, 2H); 1.96(quin, J=7.5Hz, 2H); 2.40–2.50(a.c., 4H); 2.63(t, J=5.5Hz, 2H); 3.09(m, 2H); 4.21 (t, J=7.1Hz, 2H); 5.97(m, 1H); 6.98(t, J=8.1Hz, 2H); 7.20–7.35(a.c., 4H); 7.40(m, 1H); 7.80(m, 1H); 7.89(s, 1H)(CDCl₃) |
| 31a | H | H | F | H | H | CH | N | CH=CH–CH=CH–C | 4 | HCl | 2930, 1600, 1510, 1275 | 1.70–2.00(a.c., 4H); 2.78(m, 2H); 3.20(m, 2H); 3.20–3.60(b.a., 2H); 3.81(m, 2H); 4.38(t, J=6.6Hz, 2H); 6.13 |

TABLE II-continued

| | | | | | | | | | | |
|---|---|---|---|---|---|---|---|---|---|---|
| 32a | H | CF₃ | H | CCH₃ | N | Cl | | 4 | HCl 205–206° C. | 2930, 2490, 1330, 1243, 1164, 119, 1076 KBr | (s, 1H); 7.19(t, J=8.7Hz, 2H); 7.33(m, 2H); 7.49(m, 2H); 7.71(d, J=7.8Hz, 1H); 7.77(d, J=7.6Hz, 1H); 8.79(s, 1H); 11.20(b.a., 1H)(DMSO-d₆) |
| 33a | H | H | F | H | CH | Cl | | 4 | HCl 191–192° C. | 2543, 1512, 1232, 967, 807 KBr | 1.67(m, 2H); 1.79(m, 2H); 2.33(s, 3H); 2.79(m, 1H); 2.91(m, 1H); 3.10–3.20(a.c., 3H); 3.55(m, 1H); 3.77(m, 1H); 3.91–4.00(a.c., 3H); 6.33(s, 1H); 7.58–7.80 (a.c., 4H); 11.32(b.a., 1H)(DMSO-d₆) |
| 34a | H | H | H | N | CH | CH=CH–CH=CH–C | | 4 | HCl 193–194° C. | 2931, 2566, 742 KBr | 1.71–1.85(a.c., 4H); 2.68(m, 1H); 2.86(m, 1H); 3.10–3.20(m, 2H); 3.55(m, 1H); 3.72(m, 1H); 3.90(m, 1H); 4.12(t, J=6.5Hz, 2H); 6.14(m, 1H); 7.20(t, J=8.7Hz, 2H); 7.40–7.55(a.c., 3H); 8.06(s, 1H); 11.20(b.a., 1H)(DMSO-d₆) |
| 35a | H | H | F | N | CH | Cl | | 4 | HCl 160–161° C. | 2990, 2590, 1512, 1409, 1241, 827 KBr | 1.80(m, 2H); 1.91(m, 2H); 2.67(m, 1H); 2.88(m, 1H); 3.10–3.20(a.c., 3H); 3.52(m, 1H); 3.71(m, 1H); 3.90 (m, 1H); 4.46(t, J=6.7Hz, 2H); 6.15(s, 1H); 7.14 (t, J=7.5Hz, 1H); 7.25–7.41(a.c., 4H); 7.46(d, J=8.6Hz, 2H); 7.71(d, J=8.6Hz, 1H); 7.75(d, J=8.3Hz, 1H); 8.08(s, 1H); 11.18(b.a., 1H)(DMSO-d₆) |
| 36a | H | H | H | CCH₃ | N | ![4-Cl-phenyl] | | 4 | HCl 198–199° C. | 2472, 1560, 1450, 1095, 955, 810, 745 KBr | 1.67(m, 2H); 1.79(m, 2H); 2.33(s, 3H); 2.67(m, 1H); 2.90(m, 1H); 3.10–3.25(a.c., 3H); 3.54(m, 1H); 3.72 (m, 1H); 3.85–3.98(a.c., 3H); 6.13(s, 1H); 7.19(m, 2H); 7.50(m, 2H); 11.28(b.a., 1H)(DMSO-d₆) |
| 37a | H | H | H | N | CH | ![4-Cl-phenyl] | | 4 | 126–127° C. | 2935, 1570, 1493, 1455, 1379, 1091, 953, 815, 746 KBr | 1.77(m, 2H); 1.87(m, 2H); 2.70(m, 1H); 2.86(m, 1H); 3.16(a.c., 3H); 3.55(m, 1H); 3.73(m, 1H); 3.90(m, 1H); 4.17(t, J=6.6Hz, 2H); 6.15(m, 1H); 7.25–7.47(a.c., 7H); 7.59(m, 2H); 7.90(s, 1H); 8.27(s, 1H); 10.91(b.a., 1H)(DMSO-d₆) |
| 38a | H | H | F | CH | N | H | | 4 | HCl 166–168° C. | 3450, 2429, 2707, 2593, 1512, 1437, 1230, 816, 626 KBr | 1.60(m, 2H); 1.97(m, 2H); 2.48(t, J=7.3Hz, 2H); 2.56 (m, 2H); 2.67(t, J=5.1Hz, 2H); 3.13(m, 2H); 4.18 (t, J=7.1Hz, 2H); 6.05(m, 1H); 7.23–7.40(a.c., 9H); 7.61 (s, 1H); 7.74(s, 1H)(CDCl₃) |
| 39a | H | H | F | CH | N | H | | 4 | oil | 2944, 2808, 2773, 1602, 1510, 1273, 1227, 1161, 1140, 846, 824, 681 film | 1.74(m, 2H); 1.86(m, 2H); 2.68(m, 1H); 2.84(m, 1H); 3.16(a.c., 3H); 3.53(m, 3H); 3.70(m, 1H); 3.91(m, 1H); 4.27(t, J=6.7Hz, 2H); 6.12(m, 1H); 7.19(t, J=8.9Hz, 2H); 7.50(dd, J=7.2Hz, J=5.5Hz, 2H); 8.23(s, 1H); 8.93 (s, 1H); 11.02(b.a., 1H)(DMSO-d₆) |
| 40a | H | H | F | CCH₃ | N | CH=CH–CH=CH–C | | 4 | oil | 2932, 1512, 1456, 1404, 1231, 744 film | 1.60(m, 2H); 1.97(m, 2H); 2.40–2.70(a.c., 6H); 3.12 (m, 2H); 4.22(t, J=6.9Hz, 2H); 5.99(m, 1H); 6.98(m, 2H); 7.35(m, 2H); 7.95(s, 1H); 8.07(s, 1H)(CDCl₃) |
| 41a | H | H | F | N | CH | CH=CH–CH=CH–C | | 4 | oil | 2932, 2805, 1511, 1465, 1230, 1160, 825, 752, 741 film | 1.63(m, 2H); 1.88(m, 2H); 2.42–2.55(a.c., 4H); 2.61 (s, 3H); 2.65(t, J=5.5Hz, 1H); 3.09(m, 2H); 4.14 (t, J=7.3Hz, 2H); 5.97(m, 1H); 6.99(m, 2H); 7.19–7.35 (a.c., 5H); 7.68(m, 1H)(CDCl₃) 1.57(m, 2H); 1.99(m, 2H); 2.42–2.50(a.c., 4H); 2.62 (t, J=5.6Hz, 2H); 3.06(m, 2H); 4.42(t, J=6.9Hz, 2H); 5.95 (m, 1H); 6.97(t, J=8.8Hz, 2H); 7.12(m, 1H); 7.25–7.41 (a.c., 4H); 7.71(d, J=8Hz, 1H); 7.99(s, 1H)(CDCl₃) |

TABLE II-continued

| | | | | | | | | | |
|---|---|---|---|---|---|---|---|---|---|
| 42a | H | H | H | N | C—CH=CH—CH=CH | CH | 4 | 102–103° C. | 2941, 1510, 1374, 1226, 1162, 806, 759, 741 KBr | 1.59(quin, J=7.0Hz, 2H); 2.09(quin, J=7.5Hz, 2H); 2.40–2.50(a.c., 4H); 2.64(t, J=6.2Hz, 2H); 3.10(m, 2H); 4.45(t, J=7.1Hz, 2H); 5.96(m, 1H); 6.98(t, J=8.8Hz, 2H); 7.07(t, J=7.6Hz, 1H); 7.20–7.35(a.c., 3H); 7.63 (d, J=8.5Hz, 1H); 7.71(d, J=8.6Hz, 1H); 7.90(s, 1H) (CDCl$_3$) |
| 43a | H | F | H | N | C—CH=CH—CH=CH | N | 4 | HCl 208–209° C. | 2574, 2482, 1510, 1231, 745 KBr | 1.80(m, 2H); 2.11(quin, J=7.2Hz, 2H); 2.69(m, 1H); 2.83(m, 1H); 3.10–3.20(a.c., 3H); 3.52(m, 1H); 3.71 (m, 1H); 3.88(m, 1H); 4.80(t, J=6.3Hz, 2H); 6.11(s, 1H); 7.19(m, 2H); 7.41(m, 2H); 7.50(m, 2H); 7.91(m, 2H); 11.07(b.a., 1H)(DMSO-d$_6$) |
| 44a | H | F | H | N | C—CH=CH—CH=CH | N | 4 | 76–77° C. | 2913, 1511, 1470, 1380, 1327, 1224, 1172, 1132, 851, 826, 757 KBr | 1.60(quin, J=7.5Hz, 2H); 2.19(quin, J=8.2Hz, 2H); 2.41–2.59(a.c., 4H); 2.64(t, J=5.7Hz, 2H); 3.08(m, 2H); 4.77(t, J=7.0Hz, 2H); 5.95(m, 1H); 6.97(t, J=8.8Hz, 2H); 7.25–7.40(a.c., 4H); 7.85(m, 2H)(CDCl$_3$) |
| 45a | H | F | H | N | N | CH | 4 | HCl 204–205° C. | 2928, 2680, 2573, 2559, 1515, 1454, 1272, 1242, 1224, 1166, 819, 745 KBr | 1.81(m, 2H); 1.99(m, 2H); 2.67(m, 1H); 2.84(m, 1H); 3.10–3.20(a.c., 3H); 3.53(m, 1H); 3.72(m, 1H); 3.90 (m, 1H); 4.76(t, J=6.9Hz, 2H); 6.12(s, 1H); 7.19 (t, J=8.8Hz, 2H); 7.39(t, J=7.6Hz, 1H); 7.45–7.60(a.c., 3H); 7.94(d, J=8.3Hz, 2H); 8.03(d, J=8.3Hz, 2H); 11.04 (b.a., 1H)(DMSO-d$_6$) |
| 46a | H | F | H | N | CH=CH—CH=CH | N | 4 | 88–90° C. | 2939, 1510, 1229, 1209, 1164, 744 KBr | 1.58(quin, J=7.5Hz, 2H); 2.07(quin, J=7.5Hz, 2H); 2.40–2.50(a.c., 4H); 2.61(m, 2H); 3.05(m, 2H); 4.66 (t, J=7.0Hz, 2H); 5.95(m, 1H); 6.96(t, J=8.8Hz, 2H); 7.23–7.38(a.c., 3H); 7.44(m, 1H); 7.52(m, 1H); 8.04 (d, J=8.3Hz, 1H)(CDCl$_3$) |
| 47a | H | Cl | H | N | CH=CH—CH=CH | CH | 4 | HCl 172–173° C. | 3068, 2948, 1491, 1445, 1320, 1308, 1096, 968, 809, 799 KBr | 1.71(m, 2H); 1.80(m, 2H); 2.83(m, 1H); 3.15–330(a.c., 3H); 3.44(m, 1H); 3.72(m, 1H); 3.89(m, 1H); 4.11(t, J=6.5Hz, 2H); 6.20(s, 1H); 7.41(Syst. AB, J$_{AB}$=8.8Hz, 2H); 7.48(Syst. AB, J$_{AB}$=8.8Hz, 2H); 7.52 (s, 1H); 8.04(s, 1H); 10.98(b.a., 1H)(DMSO-d$_6$) |
| 48a | H | Cl | H | N | Cl | CH | 4 | HCl 180–181° C. | 2955, 2929, 2530, 1445, 965, 761, 745 KBr | 1.70–190(a.c., 4H); 2.69(m, 1H); 2.89(m, 1H); 3.10–3.20(a.c., 3H); 3.53(m, 1H); 3.70(m, 1H); 3.91(m, 1H); 4.15(t, J=6.5Hz, 2H); 6.16(m, 1H); 6.23(m, 1H); 7.28–7.50(a.c., 6H); 7.78(m, 1H); 11.26(b.a., 1H) (DMSO-d$_6$) |
| 49a | H | H | H | N | H | N | 4 | HCl 122–123° C. | 2937, 2370, 1503, 1276, 1142, 774, 755 KBr | 1.74(m, 2H); 1.84(m, 2H); 2.72(m, 1H); 2.87(m, 1H); 3.10–3.20(a.c., 3H); 3.54(m, 1H); 3.73(m, 1H); 3.88 (m, 1H); 4.22(t, J=6.6Hz, 2H); 6.15(s, 1H); 7.27–7.70 (a.c., 3H); 7.47(m, 2H); 7.97(s, 1H); 8.59(s, 1H); 11.20 (b.a., 1H)(DMSO-d$_6$) |
| 50a | H | H | H | CPh | H | N | 4 | HCl 170–171° C. | 2930, 2554, 1465, 1459, 1444, 1278, 1075, 744, 762, 749, 732, 711, 702, 690 KBr | 1.62–1.78(a.c., 4H); 2.75(m, 2H); 3.00(m, 2H); 3.25 (m, 2H); 3.69(m, 2H); 4.08(t, J=6.7Hz, 2H); 6.13(s, 1H); 7.07(s, 1H); 7.24–7.40(a.c., 3H); 7.42–7.52(a.c., 6H); 7.62(Syst. AB, J$_{AB}$=7.6Hz, 2H)(DMSO-d$_6$) |
| 51a | H | H | H | CH | H | CH | 4 | HCl 197–199° C. | 2930, 2482, 1448, 1280, 1090, 732 KBr | 1.60–1.80(a.c., 4H); 2.70(m, 4H); 2.84(m, 1H); 3.08–3.22(a.c., 3H); 3.50(m, 1H); 3.71(m, 1H); 3.86–3.96 (a.c., 3H); 5.97(t, J=2.1Hz, 2H); 6.16(m, 1H); 6.76 (t, J=2.1Hz, 2H); 7.25–7.50(a.c., 5H); 10.74(b.a., 1H) (DMSO-d$_6$) |

TABLE II-continued

| | | | | | | | | | | |
|---|---|---|---|---|---|---|---|---|---|---|
| 52a | H | H | H | H | CH | CH | H | CH | 4 | 58–60° C. | 2928, 1498, 1280, 1262, 1137, 1087, 1060, 747, 723, 691 KBr | 1.58(m, 2H); 1.84(m, 2H); 2.47(t, J=7.5Hz, 2H); 2.58 (m, 2H); 2.68(m, 2H); 3.13(m, 2H); 3.92(t, J=7.1Hz, 2H); 6.06(m, 1H); 6.15(t, J=2.2Hz, 2H); 6.67(t, J=2.2Hz, 2H); 7.24–7.42(a.c., 5H)(CDCl₃) |
| 53a | H | H | H | H | N | CCl | H | CH=CH—CH=CH—C | 4 | oil | 2939, 1495, 1467, 1338, 745 film | 1.58(quin. J=7.6Hz, 2H); 1.99(quin, J=7.6Hz, 2H); 2.47 (m, 2H); 2.55(m, 2H); 2.65(m, 2H); 3.10(m, 2H); 4.36 (t, J=7.1Hz, 2H); 6.04(m, 1H); 7.18–7.42(a.c., 8H); 7.67 (d, J=7.6Hz, 1H)(CDCl₃) |
| 54a | H | H | H | H | N | CCl | H | CH=CH—CH=CH—C | 4 | HCl 164–165° C. | 3460, 2940, 2550, 1338, 743 KBr | 1.80(m, 2H); 1.90(m, 2H); 2.70(m, 1H); 2.87(m, 1H); 3.07–3.22(a.c., 3H); 3.52(m, 1H); 3.71(m, 1H); 3.87 (m, 1H); 4.43(t, J=6.6Hz, 2H); 6.14(s, 1H); 7.20–7.52 (a.c., 7H); 7.65(m, 1H); 7.79(m, 1H); 11.16(b.a., 1H) (DMSO-d₆) |

BIOLOGICAL TESTS

Binding to The Serotonin Receptor (5-HT$_{1A}$)

A rat hippocampus homogenate is used, a modification of the process of S. J. Peroutka, J. of Neurochem., 47(2), 529–540 (1986) being followed. [$^3$H]-8-OH-DPAT is used as radioligand and serotonin is used for measuring the non-specific binding. The incubation time is 15 minutes at a temperature of 37° C. The radioligand bound to the protein is separated by filtration on glass fiber filters and the radioactivity retained on the filter is determined by liquid scintillation. The inhibition constants ($K_i$, nM) are calculated by non-linear regression analysis by using the EBDA/LIGAND program (Munson and Rodbard, Analytical Biochemistry, 107, 220 (1980)).

Binding to the Sigma Receptor

A guinea pig brain (less the cerebellum) homogenate is used, a modification of the process of L. Radesca et al., J. Med. Chem., 34, 3058–3065 (1991) being followed. [$^3$H]-(+)-3-PPP is used as radioligand and haloperidol is used for measuring the non-specific binding. The incubation time is 120 minutes at a temperature of 25° C. The radioligand bound to the protein is separated by filtration on glass fiber filters and the radioactivity retained on the filter is determined by liquid scintillation. The inhibition constants ($K_i$, nM) are calculated by non-linear regression analysis by using the EBDA/LIGAND program (Munson and Rodbard, Analytical Biochemistry, 107, 220 (1980)).

TABLE III

BINDING

| Example | Sigma Ki (nM) | Sigma % Des (10$^{-6}$M) | 5-HT$_{1A}$ Ki (nM) | 5-HT$_{1A}$ % Des (10$^{-6}$M) |
|---|---|---|---|---|
| 1 | 6.6 | 93 | | |
| 2 | 15 | 90 | | |
| 5 | 6.4 | 94 | | 12 |
| 6 | 4.3 | 95 | | |
| 1a | 46 | 86 | 37 | 94 |
| 2a | | 82 | | 78 |
| 3a | 11 | 97 | 56 | 90 |
| 4a | 11 | 93 | 199 | 72 |
| 5a | 19 | 96 | 6.1 | 97 |
| 6a | | 91 | 9.0 | 100 |
| 7a | | 96 | 0.4 | 98 |
| 8a | | 97 | | 90 |
| 9a | | 97 | 4.6 | 100 |
| 10a | 40 | 88 | 1.3 | 100 |
| 11a | | 92 | | 93 |
| 14a | | 94 | | 94 |
| 15a | 8.4 | 94 | | 98 |
| 16a | 17 | 95 | | 86 |
| BMY 14802 | 733 | | | |

The daily dose in human medicine is between 1 milligram and 500 milligrams of product, which can be administered in one or a number of intakes. The compositions are prepared in formulae compatible with the method of administration used, such as, for example, tablets, dragées, capsules, suppositories, solutions or suspensions. These compositions are prepared by known processes and they comprise from 1 to 60% by weight of active principle (compound of general formula I) and from 40 to 99% by weight of appropriate pharmaceutical vehicle compatible with the active principle and the physical form of the composition used. By way of example, the formula of a tablet which contains a product of the invention is presented.

Example of a formula for a tablet

| | |
|---|---|
| Example 11a | 5 mg |
| Lactose | 60 mg |
| Crystalline cellulose | 25 mg |
| Povidone K 90 | 5 mg |
| Pregelatinized starch | 3 mg |
| Colloidal silicon dioxide | 1 mg |
| Magnesium stearate | 1 mg |
| Total weight | 100 mg |

We claim:

1. A method of treating a condition selected from anxiety, psychosis, epilepsy, convulsion, motoricity problems, amnesia and senile dementia comprising administering to a patient in need of such treatment, an effective amount of at least one compound having the formula

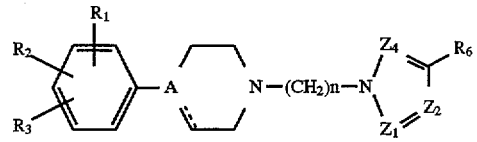

and its physiologically acceptable salts, wherein $R_1$, $R_2$, $R_3$, which are identical or different, each represent a hydrogen atom, a halogen atom, a linear or branched alkyl radical, an aryl or substituted aryl radical or an alkoxyl radical;

A represents a carbon atom and the dotted line represents an additional bond or A represents a carbon atom bonded to a hydroxyl group (C—OH) and the dotted line represents the absence of an additional bond, n can have values ranging from 2 to 6, $Z_1$ represents a nitrogen atom or a substituted carbon atom which can be represented by C—R $Z_2$ represents a nitrogen atom or a substituted carbon atom which can be represented by C—R$_5$, and $Z_4$ represents a nitrogen atom or a substituted carbon atom which can be represented by C—R$_1$, wherein all of $Z_1$, $Z_2$ $Z_4$ cannot be a nitrogen atom, where $R_4$, $R_5$, $R_6$ and $R_7$, which are identical or different, represent a hydrogen atom, a halogen atom, a linear or branched alkyl radical, a hydroxyl radical, an alkoxyl radical, a carboxyl radical, a carboxamide radical, an alkyl carboxylate radical or an aryl or substituted aryl radical.

2. The method of claim 1 wherein the compound is 4,5-dichloro-2-methyl-1-[4-(4-phenyl-1,2,3,6-tetrahydro-1-pyridyl)butyl]-1H imidazole, 4,5-dichloro-2-methyl-1-[4-(4-phenyl-1,2,3,6-tetrahydro-1-pyridyl)butyl]-1H-imidazole hydrochloride, or 4,5-dichloro-2-methyl-1[4-(4-phenyl-1,2,3,6-tetrahydro-1-pyridyl)butyl]-1H-imidazole dihydrochloride.

* * * * *

UNITED STATES PATENT AND TRADEMARK OFFICE
CERTIFICATE OF CORRECTION

PATENT NO. : 5,731,331

DATED : March 24, 1998

INVENTOR(S) : Merce-Vidal et al.

It is certified that error appears in the above-indentified patent and that said Letters Patent is hereby corrected as shown below:

Column 1, line 22, "meals" should be --mammals--.

Column 30, line 41, "C--R" should be --C--$R_4$--.

Column 30, line 46, "$Z_2$ $Z_4$" should be --$Z_2$ and $Z_4$--.

Signed and Sealed this

Sixteenth Day of March, 1999

*Attest:*

Q. TODD DICKINSON

*Attesting Officer*          *Acting Commissioner of Patents and Trademarks*